United States Patent
Ansmann et al.

(10) Patent No.: US 6,562,778 B1
(45) Date of Patent: May 13, 2003

(54) SOLUBILIZERS CONTAINING ALK(EN)YL OLIGOGLYCOSIDES AND POLYOL COMPONENTS, AND METHODS OF SOLUBILIZING USING THE SAME

(75) Inventors: Achim Ansmann, Erkrath (DE); Rolf Kawa, Monheim (DE); Holger Tesmann, Juechen (DE); Guido Baumoeller, Leichlingen (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/622,145

(22) PCT Filed: Feb. 2, 1999

(86) PCT No.: PCT/EP99/00644

§ 371 (c)(1),
(2), (4) Date: Oct. 2, 2000

(87) PCT Pub. No.: WO99/41341

PCT Pub. Date: Aug. 19, 1999

(30) Foreign Application Priority Data

Feb. 11, 1998 (DE) .......................................... 198 05 433

(51) Int. Cl.$^7$ .......................... C11D 1/825; C11D 3/37; A61K 7/00; B01F 17/34; B01F 17/56
(52) U.S. Cl. ...................... 510/470; 510/101; 510/146; 510/151; 510/417; 424/401; 424/78.08
(58) Field of Search ................................. 510/101, 146, 510/151, 417, 470; 424/401, 78.08

(56) References Cited

U.S. PATENT DOCUMENTS

| | | | | |
|---|---|---|---|---|
| 5,840,943 A | | 11/1998 | Ansmann et al. | 554/166 |
| 6,264,961 B1 | * | 7/2001 | Ansmann et al. | 424/401 |
| 6,303,109 B1 | * | 10/2001 | Foerster et al. | 424/70.31 |
| 6,391,319 B1 | * | 5/2002 | Kropke et al. | 424/401 |

FOREIGN PATENT DOCUMENTS

| | | | | |
|---|---|---|---|---|
| DE | 38 30 494 A | 3/1989 | | |
| DE | 44 20 516 A1 | 12/1995 | | |
| DE | 195 33 539 A | 3/1997 | | |
| DE | 196 43 062 A1 | 6/1997 | | |
| EP | WO 97/10049 | * 3/1997 | ........... | B01F/17/00 |
| EP | WO 98/40044 | * 9/1998 | ............. | A61K/7/00 |
| EP | WO 99/41341 | * 8/1999 | ........... | C11D/1/825 |
| FR | 2 252 840 A | 8/1975 | | |
| WO | WO95/34528 | 12/1995 | | |

OTHER PUBLICATIONS

Wekel, et al., SÖFW–Journal Seifen Öle, Fette, Wachse, vol. 124, No. 11, (Oct. 1, 1998), pp. 744, 746–748, 750 Abstract only.
Patent Abstracts of Japan, vol. 095, No. 004, (May 31, 1995) & JP 07 008781A (Taiyo Kagaku Co. Ltd.), Jan. 13, 1995.
Patent Abstracts of Japan, vol. 098, No. 004, (Mar. 31, 1998) & JP 09 315932A (Shiseido Co. Ltd.), Dec. 9, 1997.
Wekel, et al., SÖFW–Journal Seifen Öle, Fette, Wachse, vol. 124, No. 11, (Oct. 1, 1998), pp. 744, 746 & 750 Abstract Only.
Schuster, Parfümerie und Kosmetik, 65, (Nov., 1984), pp. 679–680, 682, 684 & 686 No translation.
Biermann, et al., Starch/Stärke, 45 (1993), pp. 284–288 No translation.
Salka, Cosmetics & Toiletries, vol. 108, (Mar. 1993), pp. 89–94.
Kahre, et al., SÖFW–Journal, No. 8, (1995), pp. 598, 600–601 & 604–611 No translation.
Finkel, SÖFW–Journal, 122 (Aug., 1996), pp. 543–546 & 548 Abstract Only.
"Kosmetische Färbemittel", Farbstoffkommission der Deutschen Forschungsgemeinschaft, Verlag Chemie, Wienheim, 1984, pp. 81–106. No month given. No translation.

\* cited by examiner

Primary Examiner—Yogendra N. Gupta
Assistant Examiner—Brian P. Mruk
(74) Attorney, Agent, or Firm—John E. Drach; Aaron R. Ettelman

(57) ABSTRACT

Solubilizates containing a water-insoluble substance, an aqueous phase and a solubilizer, wherein the solubilizer comprises (i) an alk(en)yl oligoglycoside; and (ii) a polyol component, are described. Methods of solubilizing water-insoluble substances with combinations of alk(en)yl oligoglycosides and polyol components are also described.

12 Claims, No Drawings

SOLUBILIZERS CONTAINING ALK(EN)YL OLIGOGLYCOSIDES AND POLYOL COMPONENTS, AND METHODS OF SOLUBILIZING USING THE SAME

BACKGROUND OF THE INVENTION

Solubilizers are used in the preparation of aqueous and aqueous-alcoholic pseudosolutions ("solubilizates") of water-insoluble substances with oil-like behavior such as, for example, essential oils or vitamins, etc. The dissolution of these substances is attributable to their solubility being greater in the surfactant micelles than in the aqueous phase. This means that above all surfactants capable of forming micelles even in low concentrations appear to be particularly suitable as solubilizers [Parf. Kosm. 65, 679 (1984)]. However, surfactants such as these always contain alkylene oxide chains which is not always desirable from the marketing perspective.

It is pointed out in this connection that the use of alkyl glucosides as emulsifiers for a range of applications is already prior art. The emulsifying and dispersing properties of polyglycerol poly-12-hydroxystearates are the subject of DE-A1 4420516 and DE-A1-19643062. Mixtures of alkyl glucosides and polyglycerol poly-12-hydroxystearates and their use as emulsifiers are described in DE-A1 19533539. However, the formation of emulsions follows a different mechanism than solubilization. Accordingly, there is nothing in the suitability of a substance as an emulsifier to suggest that it would also have solubilizing properties.

The problem addressed by the present invention was therefore to provide new solubilizers for the preparation of solubilizates which would not contain any alkylene oxide and which would provide performance results at least comparable with those of known products.

BRIEF SUMMARY OF THE INVENTION

The present invention includes the use of mixtures of glycosides and polyol esters as solubilizers for the production of solubilizates.

Accordingly, the present invention relates to the use of detergent mixtures containing
  (a) alkyl and/or alkenyl oligoglycosides and
  (b) polyol polyhydroxy-12-stearates
as solubilizers for the production of clear solubilizates.

It has surprisingly been found that mixtures of alkyl and/or alkenyl oligoglycosides and polyol polyhydroxystearates adapted to one another can be cold-mixed with water in any ratio and, in addition, also have excellent solubilizing properties. Accordingly, it is now possible in accordance with the new teaching of the invention to formulate clear pseudosolutions containing essential oils or vitamins which, hitherto, could not be obtained by other methods. This discovery is also surprising because the polyol polyhydroxystearates, although having interfacially active properties, are still mainly lipophilic in character and, accordingly, are immiscible with water in any ratio.

DETAILED DESCRIPTION OF THE INVENTION

Alkyl and/or Alkenyl Olipoalycosides

Alkyl and alkenyl oligoglycosides which form component (a) are known nonionic surfactants which correspond to formula (I):

$$R^1O\text{—}[G]_p \tag{I}$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The overviews presented by Bierman et al. in Starch/Stärke 45, 281(1993), by B. Salka in Cosm. Toil. 108, 89 (1993) and by J. Kahre in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an im-purity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Polyol poly-12-hydroxystearates

The polyol poly-12-hydroxystearates which form component (b) are known substances which are marketed by Henkel KGaA of Düsseldorf, FRG, for example under the name of "Dehymuls® PGPH". Reference is also made in this connection to International patent application WO 95/34528 (Henkel). The polyol component of the emulsifiers may be derived from substances which contain at least 2, preferably 3 to 12 and more preferably 3 to 8 hydroxyl groups and 2 to 12 carbon atoms. Typical examples are
  (a) glycerol and polyglycerol;
  (b) alkylene glycols such as, for example, ethylene glycol, diethylene glycol, propylene glycol;
  (c) methylol compounds such as, in particular, trimethylol ethane, trimethylol propane, trimethylol butane, pentaerythritol and dipentaerythritol;
  (d) alkyl oligoglucosides containing 1 to 22, preferably 1 to 8 and more preferably 1 to 4 carbon atoms in the alkyl group such as, for example, methyl and butyl glucoside;

(e) sugar alcohols containing 5 to 12 carbon atoms such as, for example, sorbitol or mannitol,
(f) sugars containing 5 to 12 carbon atoms such as, for example, glucose or sucrose;
(g) amino sugars such as, for example, glucamine.

Among the emulsifiers suitable for use in accordance with the invention, reaction products based on polyglycerol are particularly important by virtue of their excellent applicational properties. It has proved to be of particular advantage to use selected polyglycerols which have the following homolog distribution (the preferred ranges are shown in brackets):

| | |
|---|---|
| glycerols | 5 to 35 (15 to 30) % by weight |
| diglycerols | 15 to 40 (20 to 32) % by weight |
| triglycerols | 10 to 35 (15 to 25) % by weight |
| tetraglycerols | 5 to 20 (8 to 15) % by weight |
| pentaglycerols | 2 to 10 (3 to 8) % by weight |
| oligoglycerols | to 100 % by weight |

Components (a) and (b) may be mixed in a ratio of 10:90 to 90:10, preferably 25:75 to 75:25 and more preferably 40:60 to 60:40. A mixture of alkyl glucosides and polyglycerol poly-12-hydroxystearate in a ratio by weight of 1:1, which is commercially obtainable as Eumulgin® VL75, is particularly preferred. The solubilizers can make up from 1 to 25% by weight and preferably from 5 to 15% by weight of the final formulations.

Essential Oils

The substances with oil-like properties which can be solubilized as described above include, for example, the essential oils. These are understood by the expert to be perfuming substances which are obtained from plants, plant parts or even spices by physical, preferably distillation-based, process steps. Essential oils can be distinguished from the known fatty oils by a simple test: they do not leave any fatty stains behind on paper. These substances are complex mixtures of partly readily volatile alcohols, aldehydes, ketones, esters, lactones, sulfur- and nitrogen-containing compounds and hydrocarbons; most of the odor-determining constituents of essential oils are terpenes and sesquiterpenes. Typical examples of suitable essential oils are the extracts of blossoms (lavender, rose, jasmine, neroli), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Suitable synthetic or semisynthetic perfume oils are Ambroxan, eugenol, isoeugenol, citronellal, hydroxycitronellal, geraniol, citronellol, geranyl acetate, citral, ionone and methyl ionone.

Vitamins

Besides the essential oils, vitamins can also be solubilized by the mixtures of alkyl glycosides and polyglycerol esters. Typical examples are vitamins of the A group (retinol, 3,4-dehydroretinol), the B group (thiamine chloride hydrochloride, riboflavin, pyridoxine, pyridoxamine, pyridoxal, cyanocobalamin, biotin, folic acid, nicotinic acid, nicotinic acid amide, pantothenic acid), the C group (ascorbic acid), the D group (calciferol, ergocalciferol, colecalciferol) and the E group (tocopherols, tocopherol acetates). The essential oils and vitamins may be used in quantities of 0.1 to 10% by weight and preferably in quantities of 0.5 to 1% by weight, based on the solubilizates.

Auxiliaries and Additives

The solubilizates may be purely aqueous although they may also be made up as aqueous-alcoholic formulations using ethanol or isopropyl alcohol. Although the mixing ratio with water is not critical, 60 to 70% by weight alcoholic solutions are preferred and may be used, for example together with suitable skin care ingredients, as lotions for impregnating refreshing towels and as deodorant formulations, aftershaves, eau-de-toilettes and the like.

The solubilizates may also contain mild surfactants, oil components, superfatting agents, stabilizers, consistency factors, thickeners, polymers, silicone compounds, biogenic agents, antidandruff agents, film formers, preservatives, hydrotropes, solubilizers, UV filters, insect repellents, self-tanning agents, dyes and the like as further auxiliaries and additives.

Typical examples of suitable mild surfactants, i.e. surfactants with particular dermatological compatibility, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more especially 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more especially benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cycloyhexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, ring opening products of epoxidized fatty acid esters with polyols, silicone oils and/or aliphatic or naphthenic hydrocarbons.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers.

Suitable consistency factors are, above all, fatty alcohols containing 12 to 22 and preferably 16 to 18 carbon atoms and, in addition, partial glycerides. A combination of these consistency factors with alkyl oligoglucosides and/or fatty acid-N-methyl glucamides of the same chain length and/or polyglycerol poly-12-hydroxystearates is preferred. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®L Grunau), quaternized wheat polypeptides, polyethyleneimine, cationic silicone polymers such as, for example, Amodimethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 225840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar®) C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methyl phenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. Suitable stabilizers are metal salts of fatty acids such as, for example, magnesium, aluminium and/or zinc stearate. Biogenic agents in the context of the invention are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes. Suitable antidandruff agents are climbazol, octopirox and zinc pyrithione. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Montmorillonites, clay minerals, Pemulen and alkyl-modified Carbopol types (Goodrich) may be used as swelling agents for aqueous phases.

UV filters in the context of the invention are organic substances which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor and derivatives thereof, for example 3-(4-methylbenzylidene)-camphor;

4-aminobenzoic acid derivatives, preferably 4-(dimethylaminoibenzoic acid-2-ethylhexyl ester, 4-(dimethylamino)-benzoic acid-2-octyl ester and 4-(dimethylaminoybenzoic acid amyl ester;

esters of cinnamic acid, preferably 4-methoxycinnamic acid-2-ethylhexyl ester, 4-methoxycinnamic acid isopentyl ester, 2-cyano-3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy4-methoxybenzophenone, 2-hydroxy-4-methoxy4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone;

propane-1,3-diones such as, for example, 1-(4-tert.butylphenyl>3-(4'-methoxyphenylypropane-1,3-dione;

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzphehones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione or 1-phenyl-3-(4'-isopropylphenyl)-propane-1,3-dione. The UV-A and UV-B filters may of course also be used in the form of mixtures. Besides the soluble substances mentioned, insoluble pigments, i.e. finely dispersed metal oxides or salts, for example titanium dioxide, zinc oxide, iron oxide, aluminium oxide, cerium oxide, zirconium oxide, silicates (talcum), barium sulfate. and zinc stearate, may also be used for this purpose. The particles should have a mean diameter of less than 100 nm, preferably between 5 and 50. nm and more preferably between 15 and 30 nm. They may be spherical in shape although ellipsoidal particles or other non-spherical particles may also be used. Besides the two groups of primary UV filters mentioned above, secondary UV filters of the antioxidant type may also be used. Secondary UV filters of the antioxidant type interrupt the photochemical reaction chain which is initiated when UV rays penetrate into the skin. Typical examples are Superoxid-Dismutase, tocopherols (vitamin E) and ascorbic acid (vitamin C). Other suitable UV filters can be found in P. Finkel's review in SÖFW-Journal 122, 543 (1996).

In addition, hydrotropes such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formalde-hyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106, These dyes are normally used in concentrations of 0.001 to 0.1% by weight, based on the mixture as a whole.

EXAMPLES

Lavender oil was stirred in a quantity of 1% by weight into aqueous solutions of various solubilizers. The results are set out in Table 1. Example 1 correspond to the invention while Examples C1 and C2 are intended for comparison.

TABLE 1

Solubilization of lavender oil (quantities in % by weight)

| Composition/evaluation | 1 | C1 | C2 |
|---|---|---|---|
| Lavender oil | 1.0 | 1.0 | 1.0 |
| Polyglyceryl-2 Dipolyhydroxystearate (and) Lauryglucoside* | 5.0 | — | — |
| Polyglyceryl-2 Dipolyhydroxystearate | — | 5.0 | — |
| Laurylglucoside | — | — | 5.0 |
| Water | | to 100 | |
| Evaluation | Clear solubilizate | Separates, cloudy | Separates, cloudy |

*Ratio by weight 1:1

Further exemplary formulations are shown in Table 2 where formulations (A) to (C) are impregnating liquids for cleaning cloths, (D) is a deodorant formulation, (E) is an eau-de-toilette and (F) is an aftershave.

TABLE 2

Exemplary formulations

| Composition | A | B | C | D | E | F |
|---|---|---|---|---|---|---|
| Polyglyceryl-2 Dipolyhydroxystearate (and) Laurylglucoside | 9.7 | 12.5 | 9.0 | 10.0 | 14.8 | 12.5 |
| Triethyl citrate | — | — | — | 2.0 | — | — |
| Coco Glycerides | 0.5 | — | — | — | — | — |
| Lavender oil | 0.3 | — | 0.5 | 1.0 | 5.0 | 2.0 |
| Bergamot oil | — | 1.5 | — | — | — | — |
| Isoamyl p-Methoxycinnamate | — | — | — | — | — | 0.2 |
| Dimethicon Copoyol | — | — | 1.0 | 1.0 | — | 1.0 |
| Ethanol | — | — | — | 10.0 | — | 10.0 |
| Methyl paraben | 0.2 | 0.2 | 0.2 | 0.2 | 0.2 | 0.2 |
| Carbomer (+ KOH, pH 5.5) | — | — | 0.05 | — | — | — |
| Panthenol | 1.0 | 1.0 | 1.0 | — | — | 1.0 |
| Bisabolol | — | 0.2 | 0.2 | — | — | — |
| Water | | | to 100 | | | |

What is claimed is:

1. A method of solubilizing a water-insoluble substance in an aqueous phase, said method comprising:

(a) providing a solubilizer comprising (i) an alk(en)yl oligoglycoside; and (ii) a polyol component;

(b) combining the solubilizer with at least one water-insoluble substance and an aqueous phase.

2. The method according to claim 1, wherein the polyol component comprises a polyol polyhydroxystearate.

3. The method according to claim 1, wherein the polyol component comprises a polyglycerol polyhydroxystearate.

4. The method according to claim 1, wherein the alk(en)yl oligoglycoside corresponds to the general formula (I):

$$R^1O\text{—}[G]_p \qquad (I)$$

wherein $R^1$ represents an alk(en)yl radical having from about 4 to about 22 carbon atoms, G represents a sugar residue having from about 5 to about 6 carbon atoms and p is a number of from about 1 to about 10.

5. The method according to claim 1, wherein the polyol component comprises a polyglycerol polyhydroxystearate, and wherein the alk(en)yl oligoglycoside corresponds to the general formula (I):

$$R^1O\text{—}[G]_p \qquad (I)$$

wherein $R^1$ represents an alk(en)yl radical having from about 4 to about 22 carbon atoms, G represents a sugar residue having from about 5 to about 6 carbon atoms and p is a number of from about 1 to about 10.

6. The method according to claim 1, wherein the solubilizer comprises polyglycerol-2-dipolyhydroxystearate and laurylglucoside.

7. The method according to claim 1, wherein the alk(en)yl oligoglycoside and the polyol component are present in a weight ratio of from about 10:90 to about 90:10.

8. The method according to claim 5, wherein the alk(en)yl oligoglycoside and the polyglycerol polyhydroxystearate are present in a weight ratio of from about 10:90 to about 90:10.

9. The method according to claim 6, wherein the laurylglucoside and the polyglycerol-2-dipolyhydroxystearate are present in a weight ratio of from about 10:90 to about 90:10.

10. The method according to claim 1, wherein the solubilizer is present in an amount of from about 1 to about 25% by weight, based on the total weight of the solubilizate.

11. The method according to claim 1, wherein the water-insoluble Lsubstance comprises at least one component selected from the group consisting of essential oils and vitamins.

12. The method according to claim 1, wherein the at least one water-insoluble substance is present in an amount of from about 0.1 to about 10% by weight, based on the total weight of the solubilizate.

* * * * *